United States Patent [19]

Dragisic et al.

[11] Patent Number: 5,776,053
[45] Date of Patent: Jul. 7, 1998

[54] LARYNGOSCOPE BLADE WITH PROTECTIVE INSERT

[76] Inventors: Branislav M. Dragisic, 7849 Forest Hill Rd., Burr Ridge, Ill. 60525; Timothy R. Lubenow, 14 S. Oak St., Hinsdale, Ill. 60521-4215

[21] Appl. No.: 843,437

[22] Filed: Apr. 15, 1997

[51] Int. Cl.$^6$ ............................................. A61B 1/267
[52] U.S. Cl. .................................................... 600/195
[58] Field of Search ................................. 600/185, 190, 600/193, 195

[56] References Cited

U.S. PATENT DOCUMENTS

| | | |
|---|---|---|
| 3,826,248 | 7/1974 | Gobels . |
| 4,112,933 | 9/1978 | Moses . |
| 4,295,465 | 10/1981 | Racz et al. ......................... 600/195 X |
| 4,570,614 | 2/1986 | Bauman ............................. 600/193 X |
| 4,583,527 | 4/1986 | Musicant et al. . |
| 5,063,907 | 11/1991 | Musicant et al. . |
| 5,065,738 | 11/1991 | Van Dam . |
| 5,438,976 | 8/1995 | Nash ................................... 600/186 |

OTHER PUBLICATIONS

Barash et al., "Clinical Anesthesia." pp. 580–585 (3rd Ed., 1997, Lippincott–Raven, Philadelphia, PA).

Collins, "Principles of Anesthesiology," pp. 16–17, 283, 319–386 (2nd Ed., 1976, Lea & Febiger, London).

Latto et al., "Difficulties in Tracheal Intubation," pp. 75–118 (1985, Bailliere Tindall, East Sussex, England).

Rogers et al., "Principles and Practice of Anesthesiology," pp. 14, 442, 588, 1019–1033, 2392–2393, 2521–2529 (1993, Mosby–Year Book, Inc. St. Louis, Missouri).

Wylie et al., "A Practice of Anaesthesia," pp. 358–368 (1972, Lloyd–Luke (Medical Books) Ltd., Aylesbury England).

Rusch Brochure for Lyncs Fiberoptic Laryngoscope System (1995).

Rusch Brochure for Green spec Fiberoptic Laryngoscope System (1995).

Rusch Brochure for Laryngoscope Systems (1994).

*Primary Examiner*—Jeffrey A. Smith
*Attorney, Agent, or Firm*—Leydig, Voit & Mayer, Ltd.

[57] ABSTRACT

A laryngoscope blade assembly comprising a unitary blade structure provided with a cutout or recess in the vertical portion of the tongue deflector and a resilient protective insert removably and pivotably coupled to the tongue protector at its proximal and distal ends such the that insert may deflect as a force, such as that applied by a patient's teeth during intubation procedures, vertically deflects the insert into the recess.

9 Claims, 9 Drawing Sheets

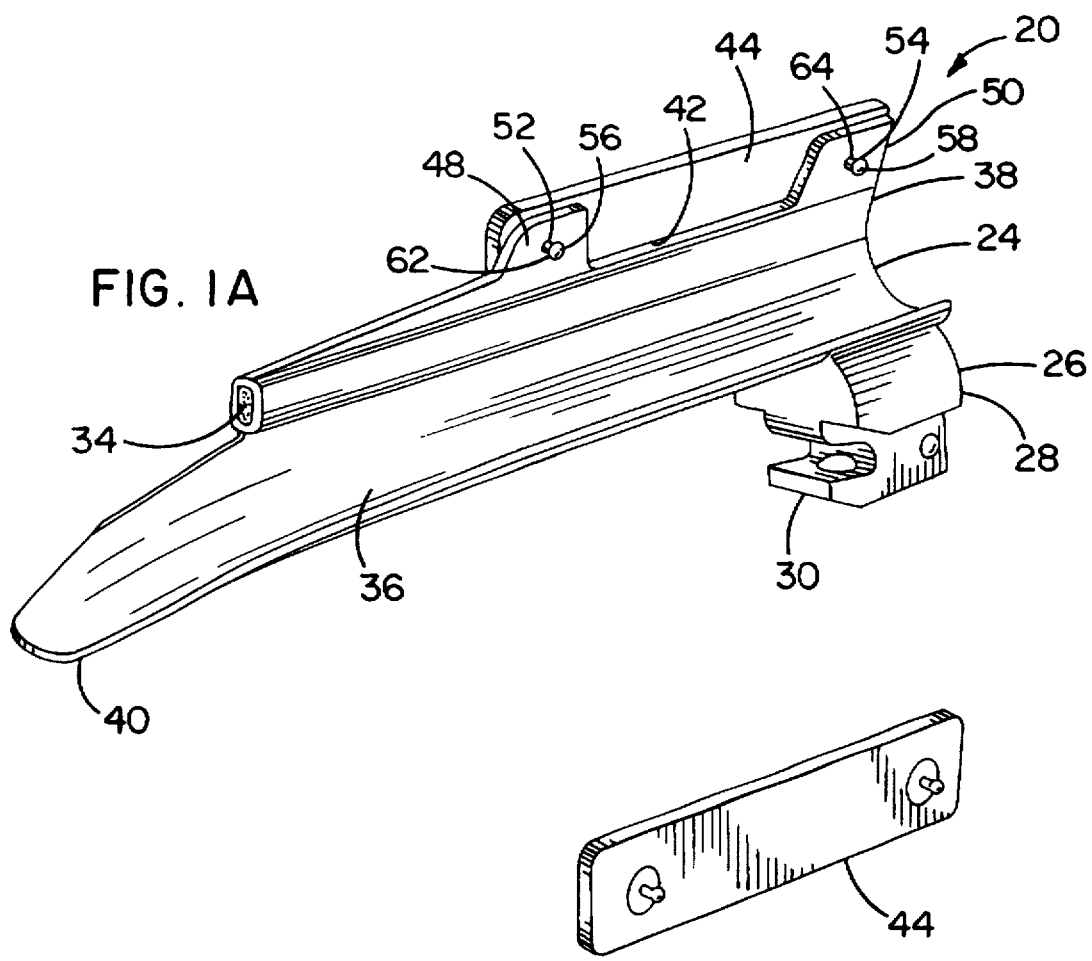
FIG. 1A
FIG. 1B
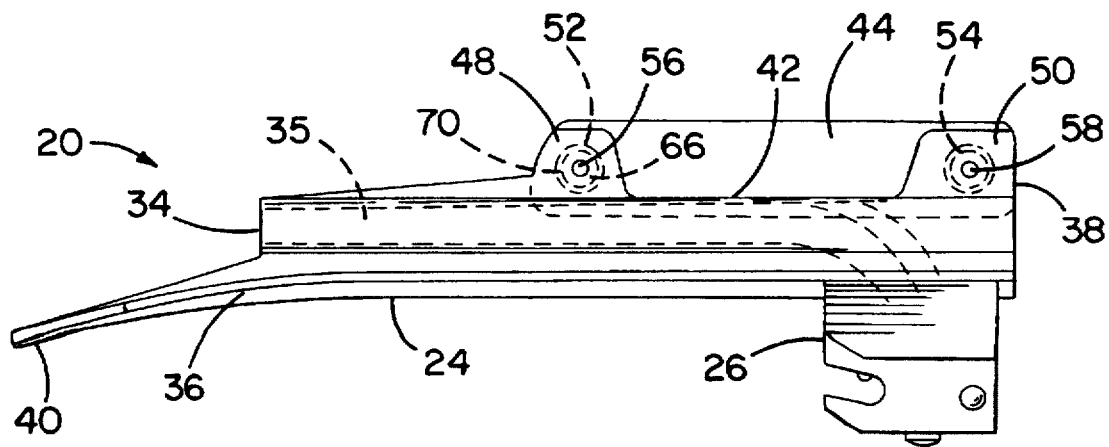
FIG. 2

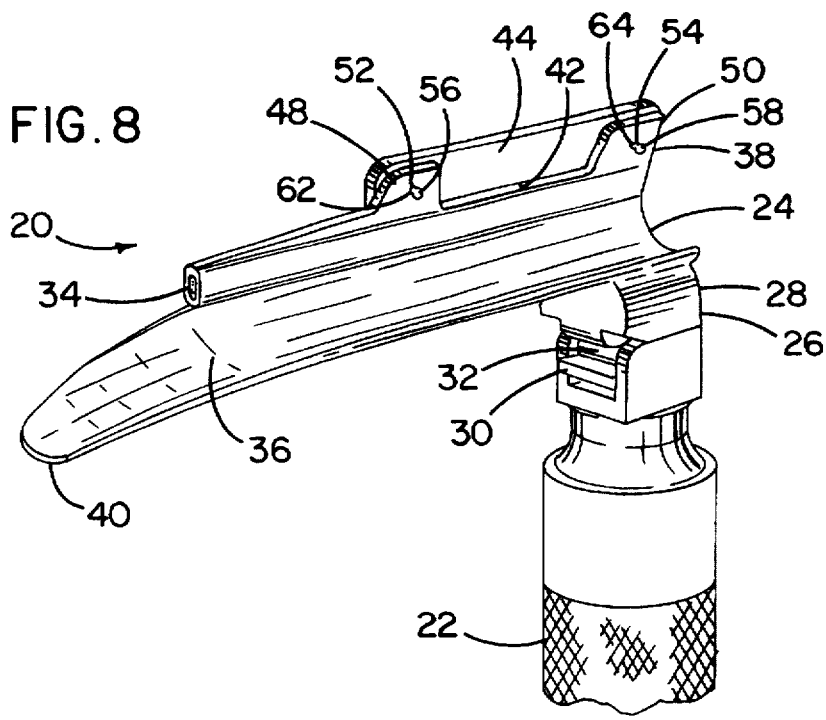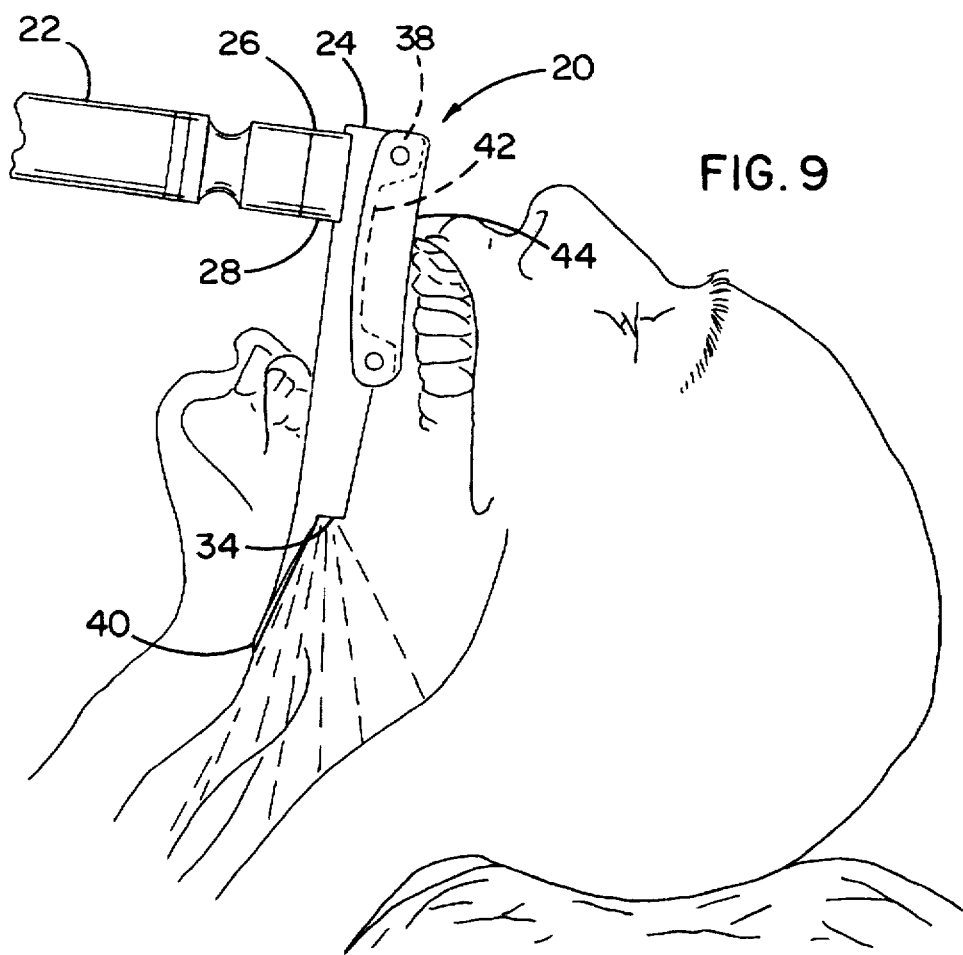

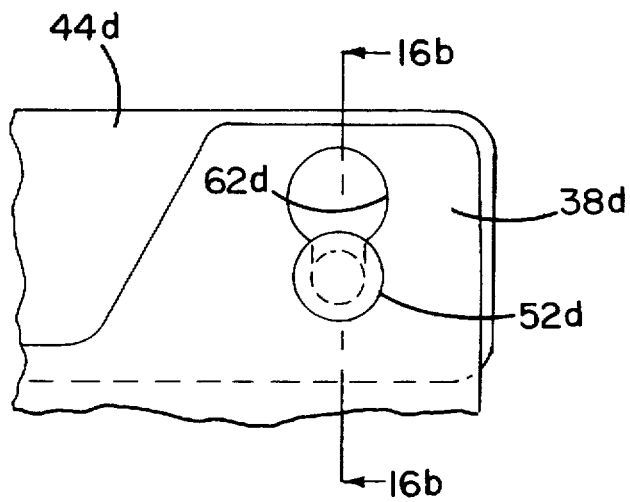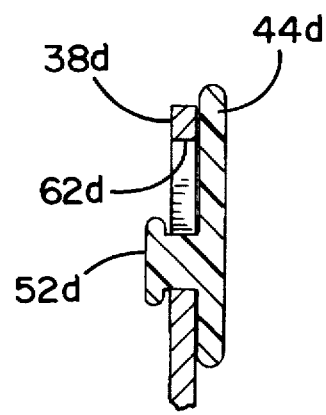
FIG. 16a
FIG. 16b
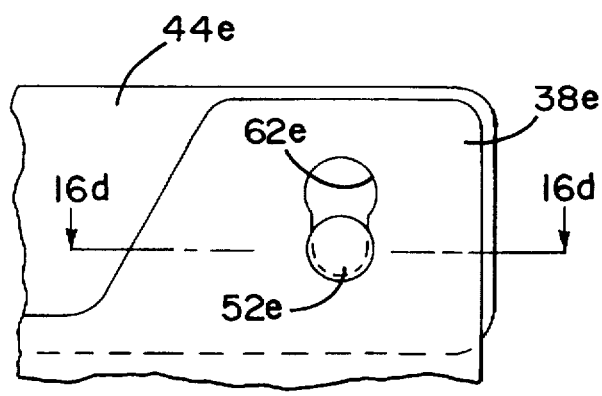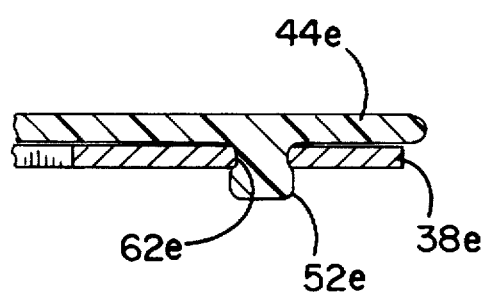
FIG. 16c
FIG. 16d

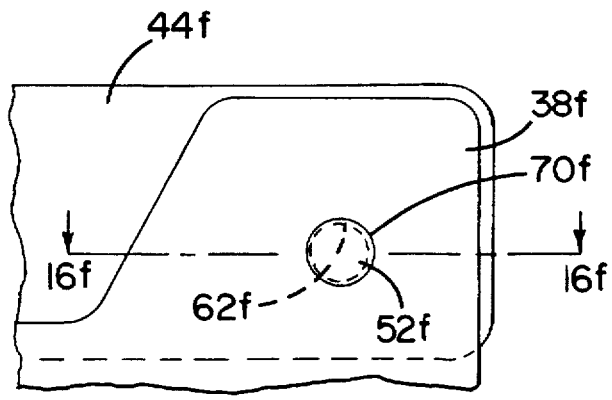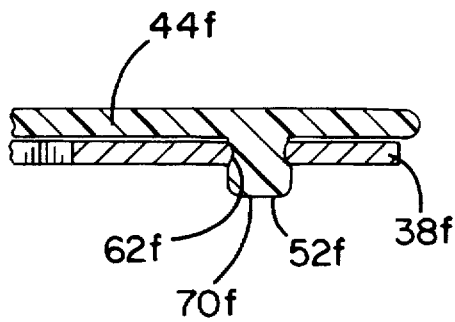
FIG. 16e　　　　　　　　FIG. 16f
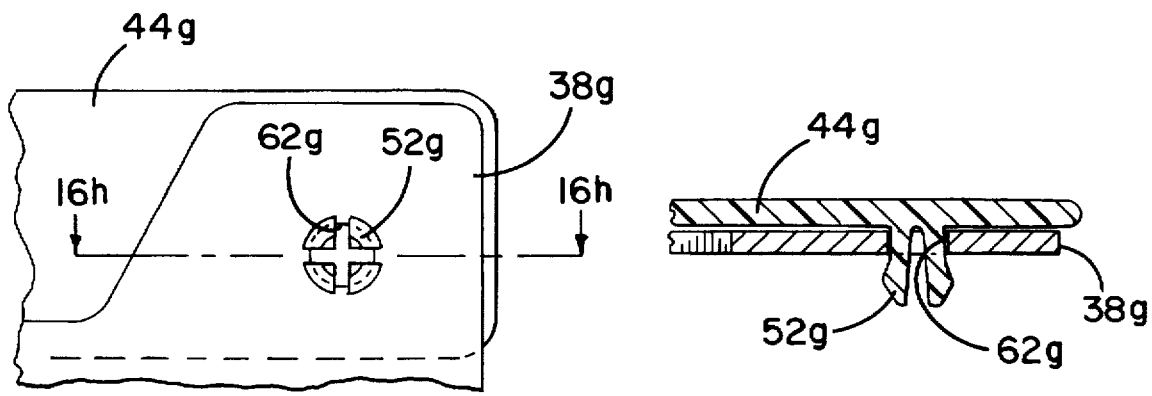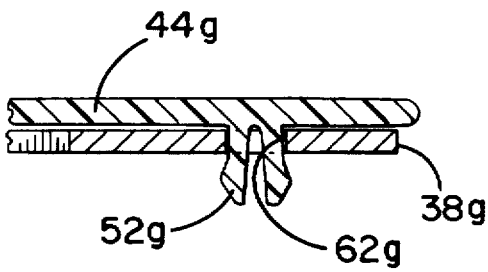
FIG. 16g　　　　　　　　FIG. 16h

LARYNGOSCOPE BLADE WITH PROTECTIVE INSERT

FIELD OF THE INVENTION

The invention relates generally to laryngoscopes, and more particularly to a laryngoscope blade having a cushioning device for minimizing the opportunity for damage to the teeth during intubation procedures.

BACKGROUND OF THE INVENTION

Laryngoscopes are generally used during intubation procedures, both in surgical and in any emergency situation requiring access to a patient's mouth and throat. Laryngoscopes are used to keep the oral cavity and glottis free for insertion of endotracheal tubes, which may facilitate positive pressure ventilation for the patient's lungs.

In order to use a laryngoscope for introduction of a tube, the patient is first moved into proper position. Preferably, the patient's head is elevated such that it gives rise to flexion of the neck with forward displacement of the pharyngeal axis. Maintaining this position, the head is extended at the atlanto-occipital joint to displace backwards the oral axis. Opening the patient's mouth as wide as possible, the laryngoscope blade is inserted in the right side of the mouth, displacing the tongue to the left as the blade is advanced. The exact position of the blade tip with respect to the epiglottis is dependent upon the type of blade utilized. Once the laryngoscope is in position and, preferably, a visual assessment made, an appropriate tube is passed along the blade and introduced through the glottis between the vocal cords into the trachea. Once the tube is in position, the laryngoscope is removed.

While laryngoscopes may be made of hard plastic, they are generally made of surgical or stainless steel or chrome plated brass. A laryngoscope comprises a handle and a blade portion. The handle portion houses a power source, generally a battery, which powers a light bulb attached to the blade portion. The light bulb illuminates the inside of a patient's mouth and throat during endotracheal intubation. In some designs, the bulb is housed within the handle, and the light carried to the blade portion via fiber optics or other light source. The blade portion generally comprises a side wall, sometimes called a tongue deflector, which assists in manipulating and moving the patient's tongue to the side of the patient's mouth to permit direct visualization of the larynx/vocal cords and placement of the endotracheal tube.

There are a number of styles of laryngoscope blades, some of which include a straight, generally flat blade and others which include a slightly curved blade. Examples of predominately straight blades which form a right angle with the laryngoscope handle include the Miller and the Wisconsin or Foregger style blades. The Miller blade is a straight blade which includes a slightly curved tip. In use, the Miller blade is placed along the laryngeal side of the epiglottis. The tip of these blades is placed on the laryngeal surface of the epiglottis and moved upwardly to elevate the epiglottis, thereby exposing the vocal cords. Examples of curved blades, which curve slightly toward the handle, are the Macintosh and Siker Mirror style blades. This type of blade is advanced into the space between the base of the tongue and the pharyngeal surface of the epiglottis. Forward and upward movement of these blades stretches the hypoepiglottic ligament to cause the epiglottis to move upward to expose the glottic opening.

The shape of the side wall of the laryngoscope blade also varies depending on the particular style of blade. Some styles comprise a generally vertical wall and horizontal flange, which may extend at a generally right angle to the side wall outwardly from the blade (as in the Macintosh style blade), or inwardly over the top of the blade (as in the Miller style blade). While the side wall and flange may form a rounded, concave shape (as with the Wisconsin or so-called Foregger style blades), the side wall necessarily includes a substantially vertical portion. Flangeless blades, although available, are not generally preferred because of increased risk of dental damage from the sharp upper edge of the deflector.

When properly positioned, a laryngoscope blade generally rests against the upper teeth of the maxilla, depending upon the individual patient's anatomy. Because the laryngoscope blade is necessarily formed of a hard, inflexible material, dental damage is a potential result of such intubation procedures. Such dental injury is typically aggravated when the upper teeth are used as a fulcrum during insertion procedures.

Various methods have been proposed to minimize such dental damage. For example, U.S. Pat. No. 3,826,248 to Gobels includes an elastic insert which is anchored within a mating opening the tongue deflector portion of the spatula by means of undercut grooves extending in cross and longitudinal directions relative to each other.

U.S. Pat. No. 4,583,527 to Musicant et al. proposed the placement of an elongated layer of soft, pliable plastic material which is adhered to the upper surface of a sheath, which is slidably and removably coupled to the flange or curved edge of the tongue deflector of a laryngoscope blade.

U.S. Pat. No. 5,063,907 to Musicant et al. is similar in that the cushioning device is an elongated clip which is formed entirely from a soft and resilient material. The cushioning clip may be removably slid onto the lateral shelf of a blade.

U.S. Pat. No. 5,065,738 to Van Dam provides a sheath which is adhered along the length of the blade, covering substantially its entire outer surface. The sheath includes a pocket at its tip and increased padding along those surface of the blade which are positioned adjacent the teeth when the blade is in position.

U.S. Pat. No. 5,438,976 to Nash provides a similar cushioning device which is adhered to the blade along a portion of its length.

The devices currently available do not satisfactorily address the need to protect a patient's teeth, as well as the needs of convenience and feasibility of use. Blade covers which are cumbersome to apply to the blade are impractical in emergency situations. Moreover, the cushioning device must be easy to remove after use and must not leave a permanent residue on the blade or the patient's teeth or mouth. While blade covers currently available are generally used only once, a laryngoscope blade is reusable and is sterilized between uses. Adhesives used in applying a blade cover to a blade often make it difficult to remove the blade cover and may leave a residue which is difficult to remove. Further, blade covers which surround the entire blade or entire flange occupy too much space in a patient's mouth, making manipulation of the laryngoscope blade and introduction of the endotracheal tube difficult.

Further, common user errors during positioning of a laryngoscope, as well as the particular structure of a given blade may cause difficulties in proper introduction of an endotracheal tube. Such errors, which include the placement of the blade at an improper depth and incomplete displacement of the tongue, may be more likely with one blade over another. For example, complete displacement of the tongue may be more difficult with blades styles wherein the flange curves back over the blade, as in the Miller and Wisconsin style blades. Moreover, in the Miller and Wisconsin styles, the actual opening for passage of the endotracheal tube is limited inasmuch as the flange curves back over the blade presenting a relatively small passageway.

OBJECTS OF THE INVENTION

It is a primary objective of the invention to provide a laryngoscope blade which minimizes or eliminates the possibility of dental damage during intubation procedures. It is a more particular objective of the invention to provide a laryngoscope blade which yields to the patient's upper teeth at a relatively predictable level of force.

Another objective of the invention is to provide a laryngoscope blade which facilitates effective deflection of the tongue and provides maximum access to the glottis. A related objective is to provide a teeth protector that occupies as little space as possible in the patient's mouth.

An additional objective is to provide a blade having a protective insert which is readily assembled and removed from the blade for easy replacement and sterilization of the blade. A related objective is to provide a protective insert which is a fully secured component of the blade, but does not require the use of an adhesive or any substance that would leave a residue on the blade after usage.

A further objective is to provide a blade which may be inserted on either the pharyngeal or laryngeal side of the epiglottis.

Yet another objective is to provide an insert and modification of existing blade designs that provides the same safety features for minimizing potential dental damage.

BRIEF SUMMARY OF THE INVENTION

In accomplishing these and other objectives, the invention provides an improved design for a laryngoscope blade assembly which minimizes or prevents possible damage to a patient's upper teeth during intubation procedures. The blade assembly includes a tongue deflector which is interrupted, or cut out along the position at which the patient's teeth are disposed when the laryngoscope is properly positioned within the patient's mouth. An elongated, thin, resilient protective insert is coupled to the tongue deflector along opposite sides of the interruption. When a force is applied to the insert, as by a patient's teeth during an intubation procedure, the insert deflects into the cutout or recessed portion of the tongue deflector.

The inventive design has a number of advantages. The insert is removably coupled to the tongue deflector, and, accordingly, may be removed for blade sterilization procedures. While the insert is preferably disposable, it may be formed of a material which may likewise be sterilized.

Further, due to the thin profile of the insert, it takes minimal additional space within the patient's mouth and does not obstruct the path of the endotracheal tube.

Moreover, because the protective insert may deflect as needed during an intubation which is more difficult due to unfavorable anatomy, it is not necessary that the blade assembly include a flange. Accordingly, the preferred embodiment of the blade includes a substantially vertical tongue deflector having no flange which might take up additional space in the patient's mouth or obstruct the pathway of an endotracheal tube. It will be appreciated, however, that the invention may be incorporated into flanged blade styles with equal success, provided that the cutout or recess interrupts the upper surface of both the flange and the vertical portion of the tongue deflector.

These and other features and advantages of the invention will be more readily apparent upon reading the following description of a preferred exemplified embodiment of the invention and upon reference to the accompanying drawings wherein:

BRIEF DESCRIPTION OF THE DRAWINGS

FIG. 1A is perspective view of a laryngoscope blade assembly in accordance with teachings of the invention.

FIG. 1B is a perspective view of the protective insert of the blade assembly of FIG. 1A.

FIG. 2 is a right plan view of the blade assembly of FIG. 1.

FIG. 8 is a perspective view of the blade assembly of FIG. 1 coupled to a laryngoscope handle.

FIG. 9 is a side view of the laryngoscope of blade assembly of FIG. 8 as properly positioned in a patient to be intubated.

FIG. 16a is a fragmentary plan view of an alternate structure for coupling the protective insert to a laryngoscope blade.

FIG. 16b is a cross-sectional view of the structure taken along line 16b—16b in FIG. 16a.

FIG. 16c is a fragmentary plan view of a second alternate structure for coupling the protective insert to a laryngoscope blade.

FIG. 16d is a cross-sectional view of the structure taken along line 16d—16d in FIG. 16c.

FIG. 16e is a fragmentary plan view of a third alternate structure for coupling the protective insert to a laryngoscope blade.

FIG. 16f is a cross-sectional view of the structure taken along line 16f—16f in FIG. 16e.

FIG. 16g is a fragmentary plan view of a fourth alternate structure for coupling the protective insert to a laryngoscope blade.

FIG. 16h is a cross-sectional view of the structure taken along line 16h—16h in FIG. 16g.

Figure 3:
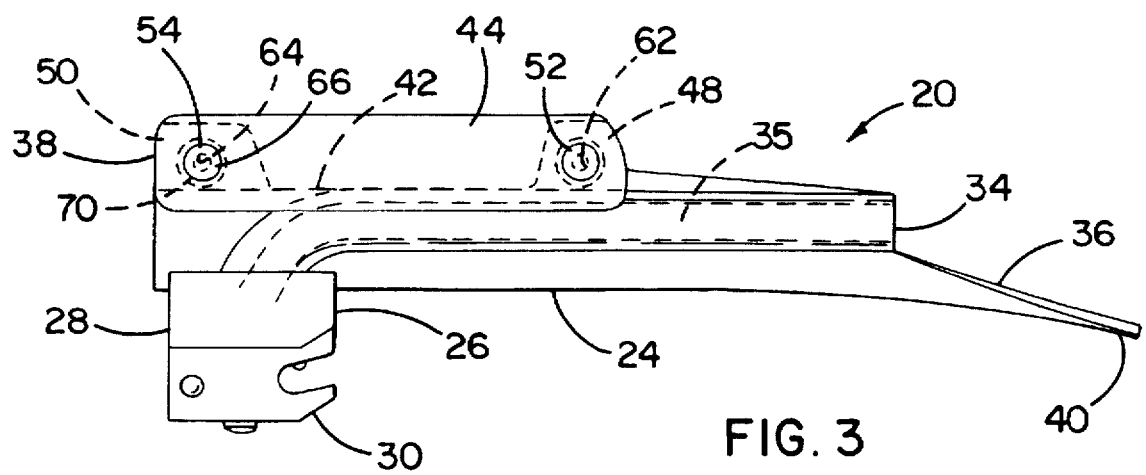
FIG. 3 is a left plan view of the blade assembly of FIG. 1.
Figure 4:
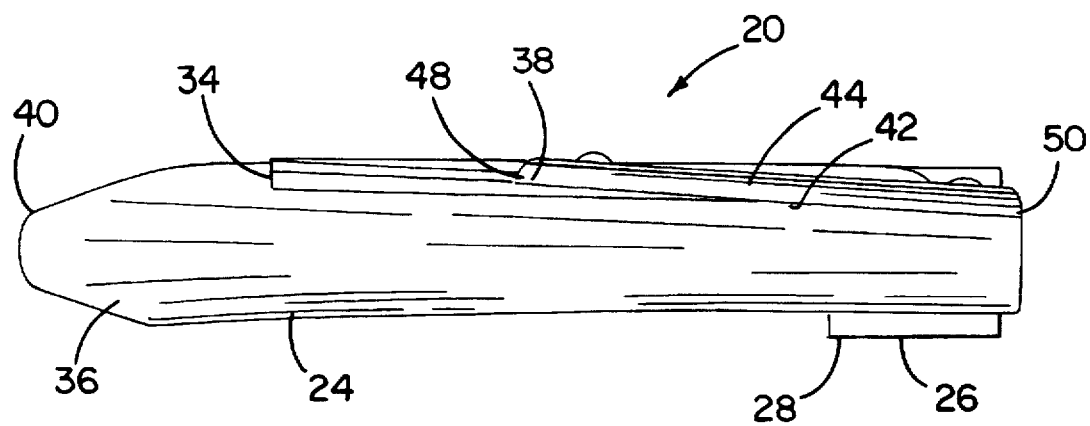
FIG. 4 is an elevational view of the blade assembly of FIG. 1.
Figure 5:
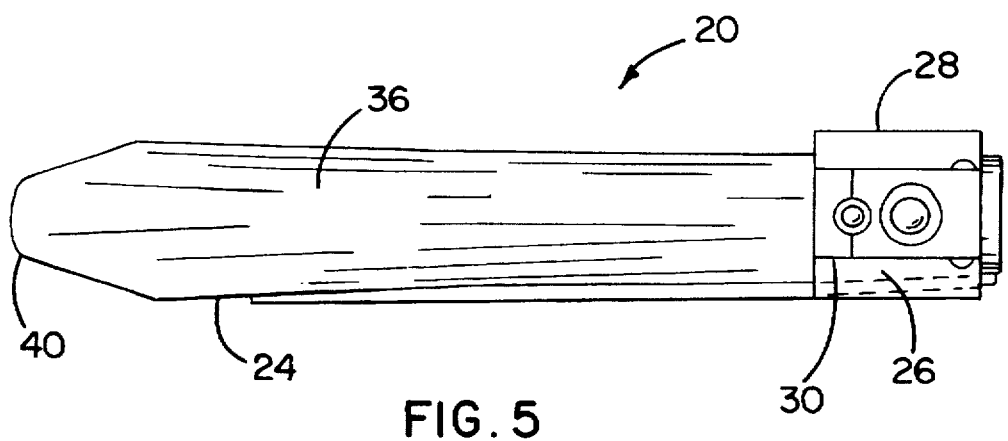
FIG. 5 is a bottom view of the blade assembly of FIG. 1.

While the invention will be described in connection with certain preferred embodiments, there is no intent to limit it to those embodiments. On the contrary, the intent is to cover all alternatives, modifications, and equivalents included within the spirit and scope of the invention as defined by the appended claims.

DESCRIPTION OF THE PREFERRED EMBODIMENTS

Turning now to the drawings, there is shown in FIGS. 1A through 9, a laryngoscope blade assembly 20 constructed in accordance with teachings of the invention, the laryngoscope blade assembly 20 shown assembled to a handle 22, which houses a power supply (not visible) generally in the form of batteries, in FIGS. 8 and 9. The blade assembly 20 comprises a unitary blade structure 24 and a base portion 26. The base portion 26 is of a conventional design, having a block 28 and a hook 30 for mating with a handle 22 in the customary manner. The handle 22 includes a pin 32 (visible in FIG. 8) which the hook 30 engages to couple the blade assembly 20 to the handle 22.

In order to illuminate the oral cavity of the patient, the laryngoscope is provided with a light. In the preferred embodiment illustrated, the light is housed in the handle 22 and is transmitted toward the end of the blade (see point 34) by fiber optics (not visible), the wiring being carried in a channel 35 (FIG. 1A) formed in the blade structure 24 and the base portion 26 (FIG. 3) although other light sources may likewise be used. As will be appreciated by those skilled in the art, the electrical connection is made when the laryngoscope blade assembly 20 is assembled onto a handle 22.

Figure 6:
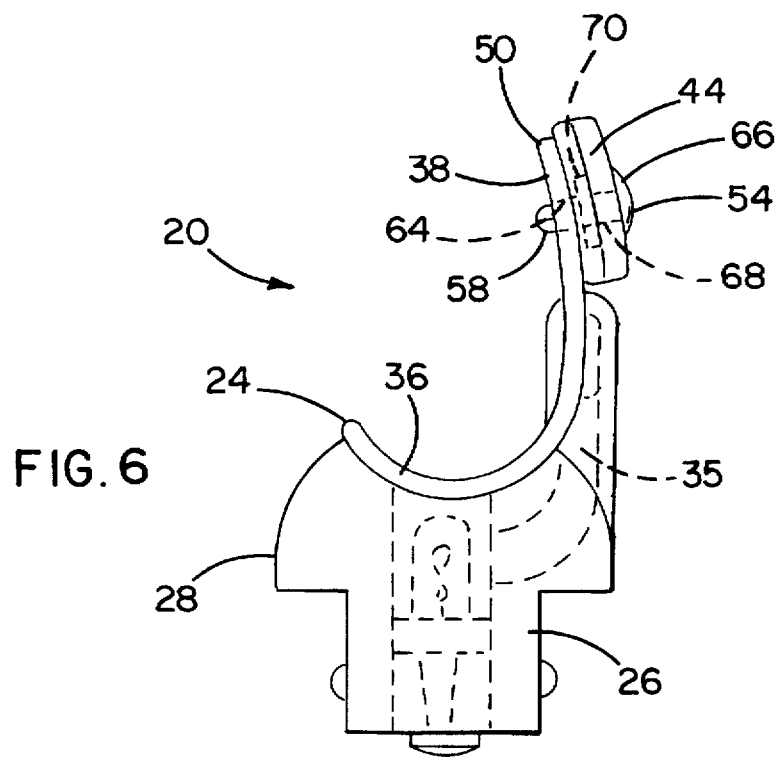
FIG. 6 is an end view of the blade assembly of FIG. 1.
Figure 7:
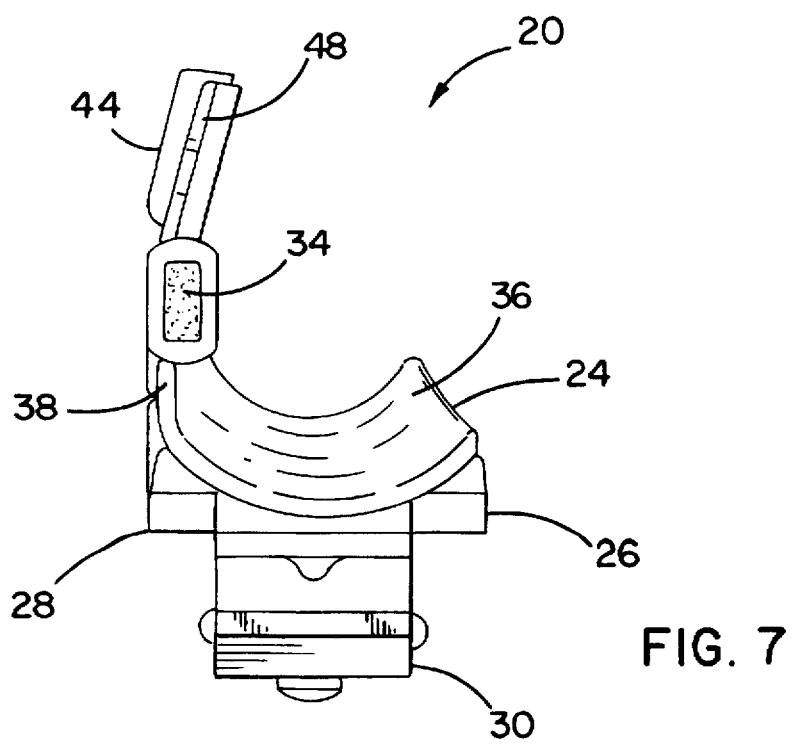
FIG. 7 is a view of the blade assembly of FIG. 1 from the opposite end as that shown in FIG. 6.

The blade structure 24 includes an elongated blade 36 and a tongue deflector 38. The blade 36 and tongue deflector 38 are formed as a single unit from a rigid material such as plastic or surgical or stainless steel. As seen most clearly in FIGS. 2 and 3, the blade 36 is substantially flat, having a slight bend downward toward the handle 22 at its distal end 40. The slight bend at the distal end 40 facilitates easy picking and lifting of the epiglottis during blade insertion. Alternately, the distal end may be placed along the pharyngeal side of the epiglottis, as with Macintosh blades. The tongue deflector 38 extends upward from the blade 36 in a smooth arc at a substantially right angle, as shown in FIGS. 6 and 7. Those skilled in the art will appreciate that the curve of the blade structure 24 is substantially more open than those of the Miller or Wisconsin style blades, and, accordingly, facilitates easy passage and placement of an endotracheal tube.

In accordance with an important aspect of the invention, the blade structure 24 is provided with means for protecting the patient's upper teeth from damage during intubation procedures. The tongue deflector 38 includes an elongated opening 42 along which a protective insert 44 is disposed. During use, the elongated opening 42 and protective insert 44 are disposed adjacent the patient's upper teeth 46, as shown in FIG. 9. Further, when the laryngoscope blade assembly 20 is properly positioned within the patient's glottis, the patient's teeth 46 may bear down on the resilient protective insert 44, minimizing any possibility of damaging the patient's dentition. Those skilled in the art will note that, when used in an educational atmosphere, a student will know when the laryngoscope blade assembly 20 is in proper position for insertion of an endotracheal tube, inasmuch as the resilient protective insert 44 of a properly sized blade 36 will be disposed adjacent the patient's upper teeth 46.

According to another important aspect of the invention, the protective insert 44 is made of a resilient material, preferably a polymeric or rubber material, and has an flat, substantially rectangular shape. The protective insert 44 is coupled to the tongue deflector 38 at its distal and proximal ends 48, 50. This unique structure of the insert 44, as well as the method of coupling the protective insert 44 to the tongue deflector 38, provide for a particularly effective method of protecting the patient's teeth. As the patient's upper teeth bear down on the insert 44, the central section of the insert 44 may deflect as shown in FIG. 9, while still providing effective support. To facilitate this flexure, the method of attaching the protective insert 44 to the tongue deflector 38 preferably permits some minor movement of the insert 44 relative to the deflector 38.

It will thus be appreciated by those in the art that the structure of the protective insert 44 and its relationship to the tongue deflector 38 facilitates the inclusion of a tongue deflector 38 which is substantially vertical to the blade 36 of the blade assembly 20, while still providing effective protection to the patient's teeth. The inclusion of a vertical tongue deflector having no flange, either inwardly or outwardly extending, results in highly effective deflection of the tongue, while providing open, clear access to the glottis and/or vocal cords. Further, the thin structure of both the tongue deflector 38 and the protective insert 44, the laryngoscope blade assembly 20 occupies a minimal amount of space within the patient's mouth, providing a clear passage for the endotracheal tube during intubation.

In order to facilitate sterilization of the blade assembly 20, the protective insert 44 is removably coupled to the tongue deflector 38. In the currently preferred embodiment, the protective insert 44 is coupled to the tongue deflector 38 by snaps 52, 54, as seen most clearly in FIGS. 1A, 1B and 6. The snaps 52, 54 include enlarged bulbs 56, 58 which are interference fit with mating openings 62, 64 in the tongue deflector 38. In this way, the protective insert 44 may be "snapped" onto the tongue deflector 38. The snaps 52, 54 and openings 62, 64 provide a structure of coupling the protective insert 44 to the tongue deflector 38 which is secure, yet the protective insert 44 is readily removable to permit sterilization of the blade assembly 20 by conventional methods.

The snaps 52, 54 themselves include two components, a male rivet portion 66 and a female bulb portion 70. The snaps 52, 54 are assembled to the protective insert 44 by mating the extension 68 of the male rivet portion 66, disposed along one side of the protective insert 44, with the interior of the bulb 56, 58 of the female bulb portion 70, disposed along the opposite side of the protective insert 44. By the force of the assembly process, the extension 68 is then deformed within the bulb 56, 58 to couple the components 66, 70 of the snap 52, 54 together.

It will be appreciated that this method of protecting the patient's teeth is equally applicable to other blade styles, including those wherein the tongue deflector includes a flange extending either inwardly or outwardly from the vertical portion of the tongue deflector. According to an important aspect of the invention, however, the surfaces of both the vertical portion of the tongue deflector and the flange must be interrupted such that the protective insert may be vertically deflected as the patient's teeth bear down on the protective insert.

For the reader's convenience, when describing alternate embodiments of the invention, as they pertain to such different blade styles, the same identification numbers as those used with the preferred embodiment of the invention, followed by the letters "a," "1b" and "c" will be used. The vertical portions of the tongue deflectors 38a, 38b, and 38c will be referenced as 37a, 37b, and 37c, while the flanges will be referenced as 39a, 39b, and 39c.

Figure 10:
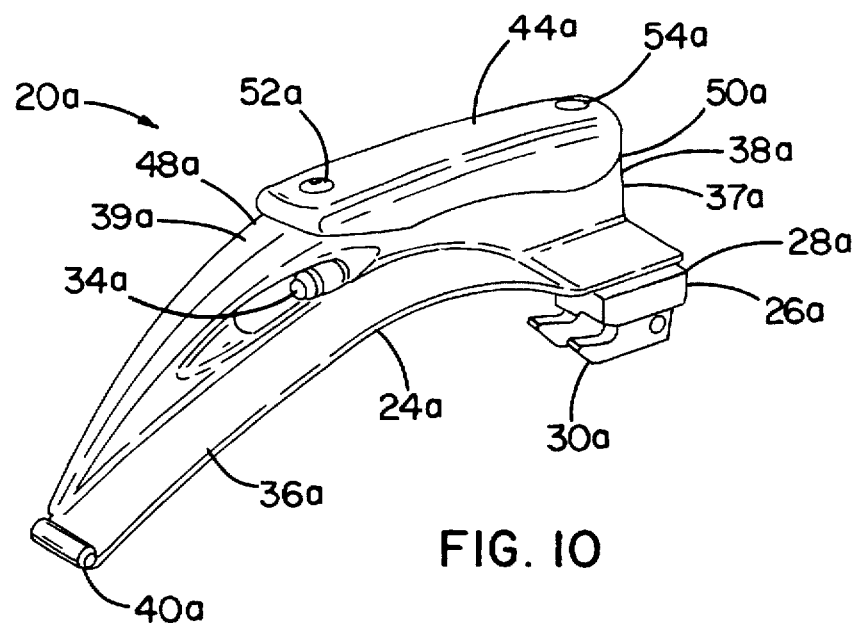
FIG. 10 is a perspective view of an alternate embodiment of a laryngoscope blade assembly constructed in accordance with teachings of the invention.
Figure 11:
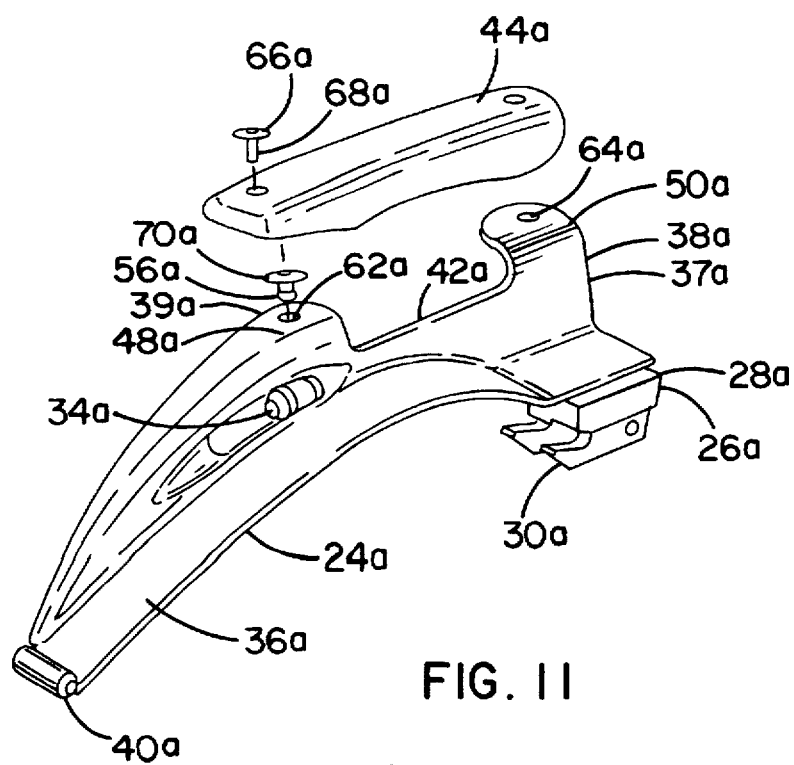
FIG. 11 is an exploded perspective view of the embodiment shown in FIG. 10.
Figure 12:
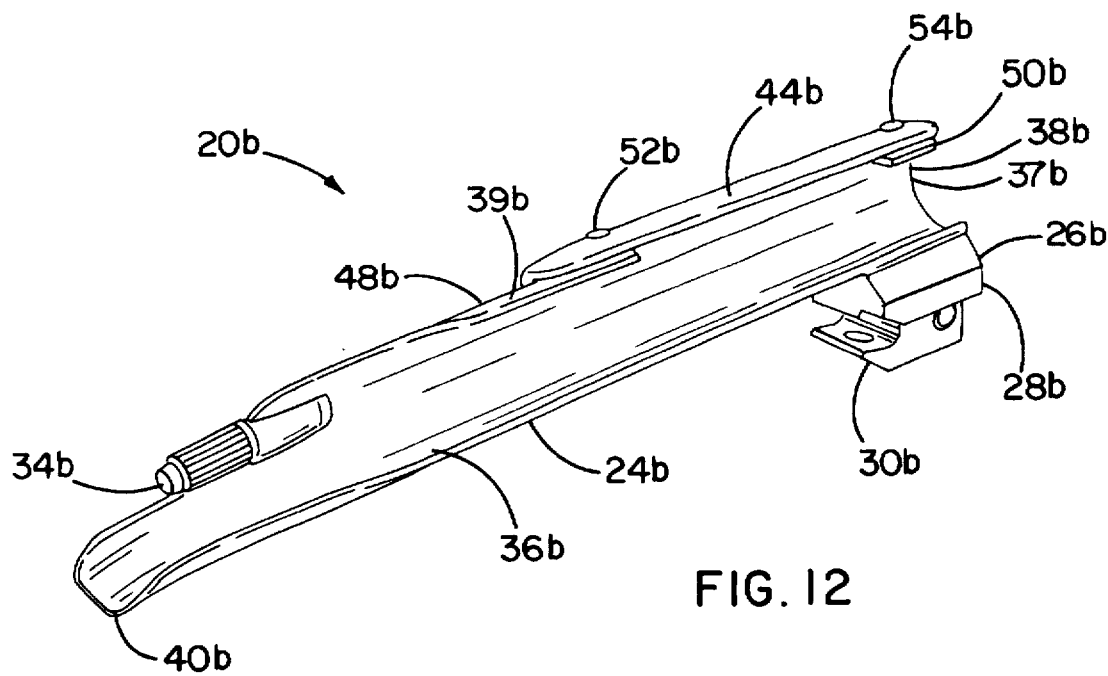
FIG. 12 is a perspective view of a second alternate embodiment of a laryngoscope blade assembly constructed in accordance with teachings of the invention.
Figure 13:
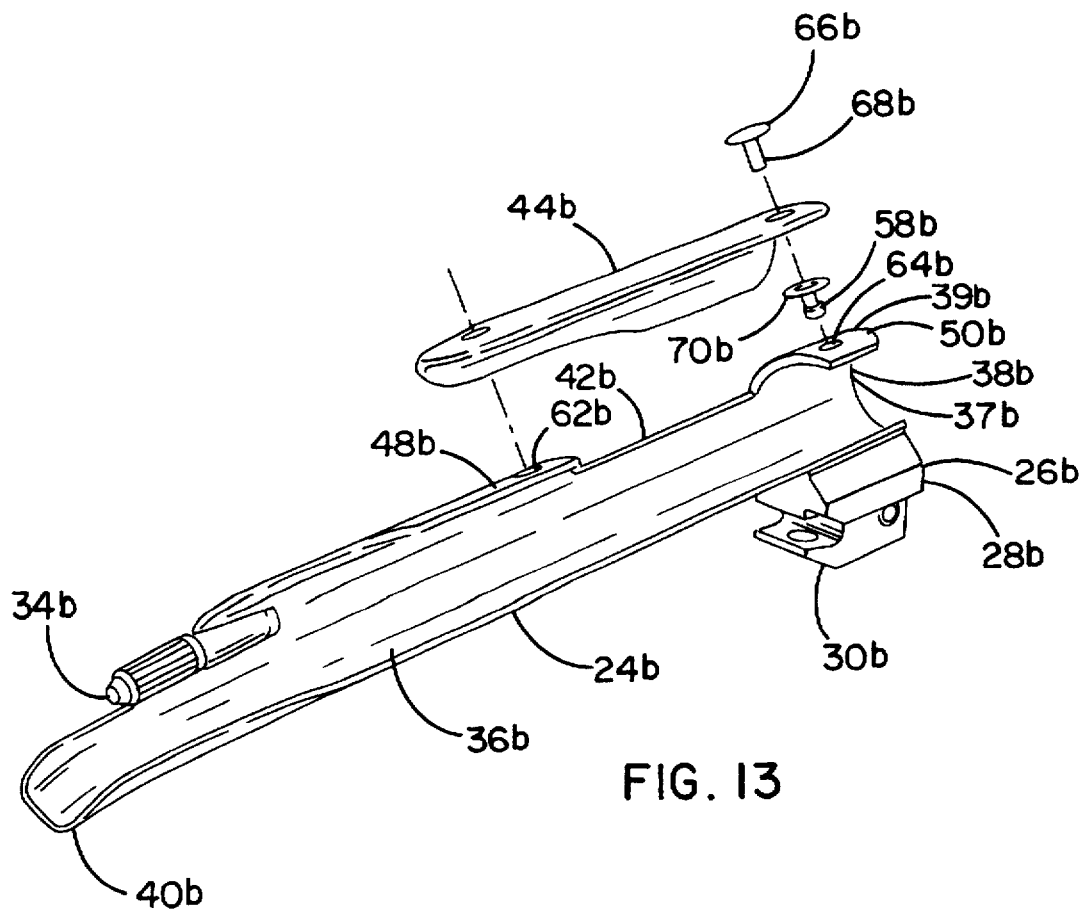
FIG. 13 is an exploded perspective view of the embodiment shown in FIG. 12.
Figure 14:
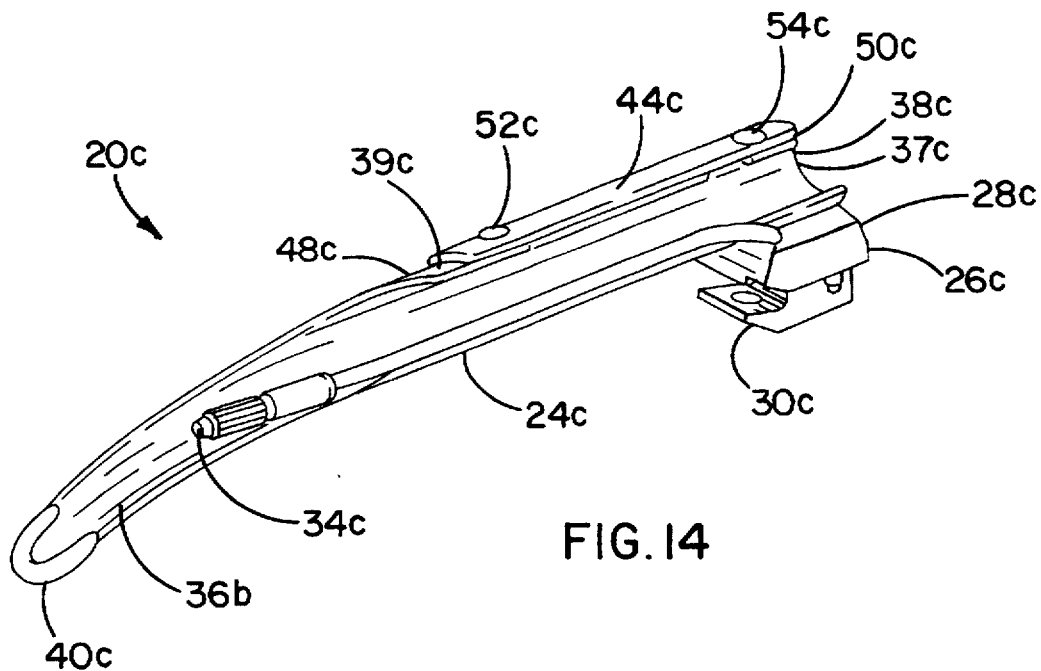
FIG. 14 is a perspective view of a third alternate embodiment of a laryngoscope blade assembly constructed in accordance with teachings of the invention.
Figure 15:
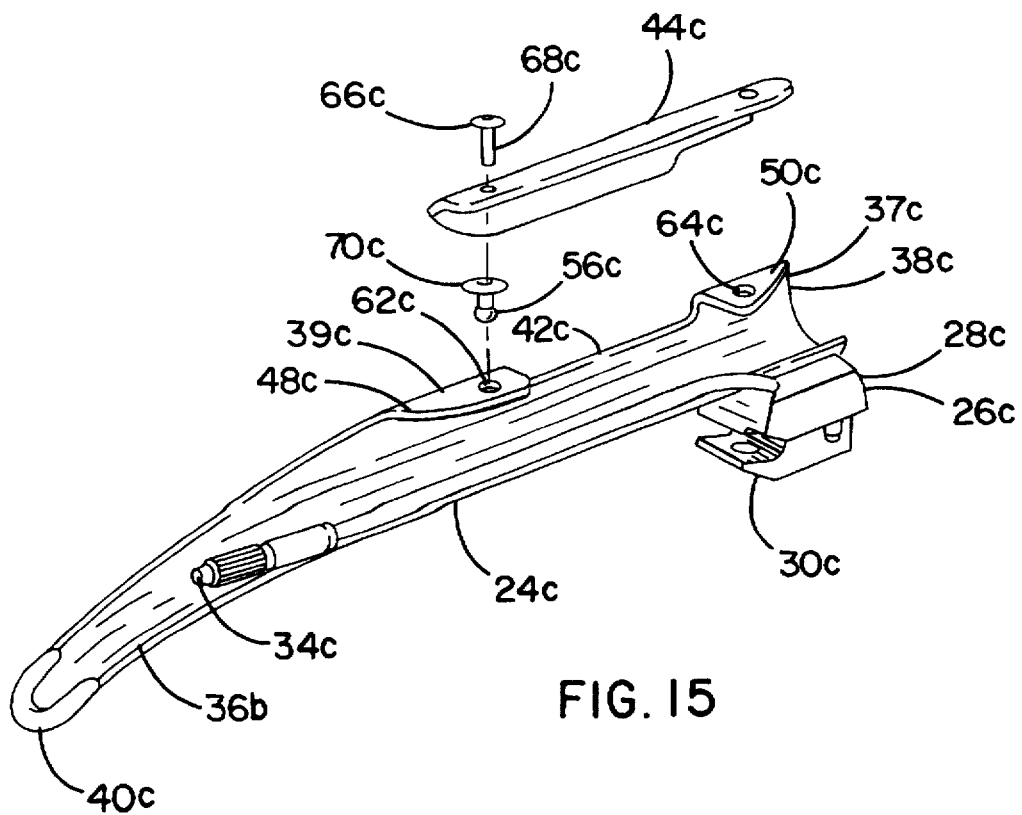
FIG. 15 is an exploded perspective view of the embodiment shown in FIG. 14.

The Macintosh blade style may be modified to include a protective insert 44a and tongue deflector 38a constructed in accordance with teachings of the invention (see FIGS. 10 and 11). To provide sufficient travel for the protective insert 44a during use, the tongue deflector 38a has been modified to include an opening 42a in its central portion. As seen most readily in FIG. 11, both the outwardly extending flange 39a, as well as the vertical portion 37a of the tongue deflector 38a are "cut out" or interrupted to provide a recess 42a. During use, the patient's teeth bear down on the protective insert 44a, which may then be deflected into the opening 42a in the tongue deflector 38a.

The protective insert 44a is removably coupled to the tongue deflector 38a at its distal and proximal ends 48a, 50a. As with the preferred embodiment of the invention, a rivet 66a and bulb portion 70a are assembled through the protective insert 44a, the bulb 66a of the snap 52a may then be removably coupled to the flange 39a by means of the opening 62a therein.

As with the Macintosh style blade of FIGS. 10 and 11, the Wisconsin and Miller style blades, which have inwardly extending flanges 39b, 39c may likewise be modified to include protective inserts 44b, 44c constructed in accordance with teachings of the invention (see FIGS. 12 and 13, and FIGS. 14 and 15, respectively). As may be seen in the drawings, both the inwardly extending flange 39b, 39c, and the substantially vertically extending portion 37b, 37c of the tongue deflectors 38b, 38c are cut out to provide travel for the protective inserts 44b, 44c should the patient's teeth bear down on the laryngoscope blade during use.

While the coupling means have been described with regard to a snap structure, alternate structures for coupling the protective insert 44 to the tongue deflector 38 are contemplated by the invention. For example, the protective insert 44d may be provided with button-like structures 52d having a small diameter stem with a relatively larger diameter head which insert and slidingly mate with keyhole-shaped opening 62d in the tongue deflector 38d as shown in FIGS. 16a and 16b. (As with the alternate blade styles described above, the same identification numbers followed by the letters "d," "e," "f," and "g" will be used to identify similar components.)

Alternately, the protective insert may be provided with a post 52e which has a slightly larger diameter than the small portion of the keyhole-shaped opening 62e, as shown in FIGS. 16c and 16d. In this way, the post 52e may be inserted into the larger portion of the keyhole-shaped opening 62e and then forced sideways into the smaller portion of the keyhole-shaped opening 62e.

In a third alternate embodiment, a snap-like structure 52f is formed directly onto the plastic of the protective insert 44f, as shown in FIGS. 16e and 16f. The female bulb portion 70f of the snap 52f is only slightly larger than the opening 62f such that the protective insert 44f may be easily snapped into position in a manner similar to that shown in FIGS. 1a through 15.

Alternately, the snap 52g may have a sectioned structure, such as is shown in FIGS. 16g and 16h. It will be appreciated that in this embodiment, the sections of the snap 52g are resilient such that they may be elastically deformed as the snap 52g is progressed through the opening 62g and then return to their original expanded position to secure the protective insert 44g to the tongue deflector 38g.

From the foregoing, it will be appreciated by those skilled in the art that alternate attachment means may be utilized. It is our intention to likewise cover those alternate attachment means.

In summary, the invention provides a design for a laryngoscope blade assembly which minimizes or prevents possible damage to a patient's upper teeth during intubation procedures. The blade assembly includes a tongue deflector which is interrupted, or recessed along the position at which the patient's teeth are positioned when the laryngoscope is properly positioned within the patient's oral cavity. An elongated, thin, resilient protective insert is removably coupled to the tongue deflector along opposite sides of the recess, and may be removed for sterilization procedures. The thin profile of the insert takes minimal additional space within the patient's mouth and does not obstruct the path of the endotracheal tube. Moreover, because the protective insert may deflect if the patient's teeth bear down during an intubation procedure, it is not necessary that the blade assembly include a flange. Although the invention may be incorporated into flanged blade styles, the preferred embodiment of the blade includes a substantially vertical tongue deflector having no flange which might take up additional space in the patient's mouth or obstruct the pathway of an endotracheal tube.

I claim as my invention:

1. A blade assembly for a laryngoscope including a handle, said blade assembly comprising base for coupling to the handle, and unitary blade structure secured to the base, said unitary blade structure including an elongated blade and a tongue deflector, said elongated blade having a proximal end, a distal end, an upper surface, a lower surface, and an elongated edge section, said lower surface of the blade being secured to the base at the proximal end, said tongue deflector extending in a direction substantially vertical to the upper surface of the elongated blade along a portion of the elongated edge section, the tongue deflector having a recess in its upper surface such that the tongue deflector is not continuous in a plane substantially parallel to the upper surface of the elongated blade, a resilient protective insert having a thin elongated shape with proximal and distal ends, the insert being removably coupled to the tongue deflector at its proximal and distal ends, the insert being disposed substantially adjacent to the recess such that the insert presents a continuous upper surface in the plane substantially parallel to the upper surface of the elongated blade, whereby a vertical force applied to the upper surface of the resilient protective insert deflects the insert within the recess.

2. The blade assembly of claim 1 wherein the unitary blade has an open oval structure, the tongue deflector being disposed in a plane substantially normal to a plane substantially containing the elongated blade.

3. The blade assembly of claim 2 wherein the protective insert is pivotably coupled to the tongue deflector at proximal and distal connections at its proximal and distal ends such that the resilient protective insert may pivot about the proximal and distal connections as the force is applied to the protective insert.

4. The blade assembly of claim 3 wherein the tongue deflector comprises a bore at its proximal and distal ends for connecting the proximal and distal connections of the protective insert, and the proximal and distal connections of the protective insert include at least one bulb which protrudes from a surface of the protective insert, the bulb engaging at least one of the bores to couple the protective insert to the tongue deflector.

5. The blade assembly of claim 1 wherein the tongue deflector includes a vertically extending portion and a substantially horizontally extending flange, the horizontally extending flange being disposed along an edge of the vertically extending portion opposite the elongated edge of the blade, the recess interrupting the flange and the vertically extending portion of the tongue deflector.

6. The blade assembly of claim 5 wherein the protective insert is pivotably coupled to the flange at proximal and distal connections at its proximal and distal ends such that the resilient protective insert may pivot about the proximal and distal connections as the force is applied to the protective insert.

7. The blade assembly of claim 6 wherein the flange comprises a bore at its proximal and distal ends for connecting the proximal and distal connections of the protective insert, and the proximal and distal connections of the protective insert include at least one bulb which protrudes from a surface of the protective insert, the bulb engaging at least one of the bores to couple the protective insert to the flange.

8. The blade assembly of claim 1 wherein the protective insert is pivotably coupled to the tongue deflector at proximal and distal connections at its proximal and distal ends such that the resilient protective insert may pivot about the proximal and distal connections as the force is applied to the protective insert.

9. The blade assembly of claim 8 wherein the tongue deflector comprises a bore at its proximal and distal ends for connecting the proximal and distal connections of the protective insert, and the proximal and distal connections of the protective insert include at least one bulb which protrudes from a surface of the protective insert, the bulb engaging at least one of the bores to couple the protective insert to the tongue deflector.

* * * * *